US009837613B2

(12) United States Patent
Mitchell et al.

(10) Patent No.: US 9,837,613 B2
(45) Date of Patent: *Dec. 5, 2017

(54) CONJUGATED POLYMERS

(71) Applicant: Merck Patent GmbH, Darmstadt (DE)

(72) Inventors: William Mitchell, Chandler's Ford (GB); Steven Tierney, Southampton (GB); Nicolas Blouin, Southampton (GB); Frank Egon Meyer, Winchester (GB); Miguel Carrasco-Orozco, Winchester (GB)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,917

(22) Filed: Jun. 5, 2015

(65) Prior Publication Data
US 2015/0270490 A1 Sep. 24, 2015

Related U.S. Application Data

(62) Division of application No. 13/820,310, filed as application No. PCT/EP2011/003952 on Aug. 5, 2011, now Pat. No. 9,153,784.

(30) Foreign Application Priority Data

Sep. 4, 2010 (EP) .................................... 10009200

(51) Int. Cl.
| | | |
|---|---|---|
| H01L 51/00 | (2006.01) | |
| C08G 75/32 | (2006.01) | |
| C07D 285/14 | (2006.01) | |
| B82Y 10/00 | (2011.01) | |
| C08G 61/12 | (2006.01) | |
| C07D 417/14 | (2006.01) | |
| H01L 51/05 | (2006.01) | |
| H01L 51/42 | (2006.01) | |
| H01L 51/50 | (2006.01) | |

(52) U.S. Cl.
CPC .......... H01L 51/0043 (2013.01); B82Y 10/00 (2013.01); C07D 285/14 (2013.01); C07D 417/14 (2013.01); C08G 61/123 (2013.01); C08G 61/126 (2013.01); C08G 75/32 (2013.01); H01L 51/0036 (2013.01); C08G 2261/12 (2013.01); C08G 2261/124 (2013.01); C08G 2261/1412 (2013.01); C08G 2261/18 (2013.01); C08G 2261/3223 (2013.01); C08G 2261/3243 (2013.01); C08G 2261/3246 (2013.01); C08G 2261/414 (2013.01); C08G 2261/51 (2013.01); C08G 2261/91 (2013.01); H01L 51/0037 (2013.01); H01L 51/0047 (2013.01); H01L 51/0512 (2013.01); H01L 51/42 (2013.01); H01L 51/4253 (2013.01); H01L 51/5012 (2013.01); Y02E 10/549 (2013.01)

(58) Field of Classification Search
CPC ..... H01L 51/0036; H01L 51/00; C09G 75/32; C07D 285/14; C08G 75/32
USPC .......................... 252/500; 526/240; 548/126
See application file for complete search history.

(56) References Cited

U.S. PATENT DOCUMENTS

| | | | | |
|---|---|---|---|---|
| 5,523,311 | A * | 6/1996 | Schurter | ................ A01N 43/82 514/361 |
| 5,766,833 | A * | 6/1998 | Suematsu | .............. G03C 1/067 430/477 |
| 6,854,544 | B2 | 2/2005 | Vide | |
| 7,772,485 | B2 | 8/2010 | Gaudiana | |
| 8,173,766 | B2 * | 5/2012 | Tierney | ................ C08G 61/122 528/211 |
| 8,269,099 | B2 * | 9/2012 | Kitazawa | ............... B82Y 10/00 136/263 |
| 8,298,685 | B2 | 10/2012 | Moriwaki | |
| 8,334,456 | B2 * | 12/2012 | Zhu | ........................ B82Y 10/00 136/263 |
| 8,530,889 | B2 | 9/2013 | Jo | |
| 8,968,885 | B2 * | 3/2015 | Brown | ................. C07D 487/04 257/40 |
| 9,153,784 | B2 * | 10/2015 | Mitchell | ............. H01L 51/0043 |
| 2004/0002576 | A1 | 1/2004 | Oguma et al. | |
| 2007/0003783 | A1 | 1/2007 | Morishita et al. | |
| 2009/0302748 | A1 | 12/2009 | Nakatani et al. | |
| 2010/0006154 | A1 * | 1/2010 | Kitazawa | ............... B82Y 10/00 136/263 |
| 2010/0024860 | A1 * | 2/2010 | He | ...................... H01L 51/0043 136/244 |

(Continued)

FOREIGN PATENT DOCUMENTS

| | | |
|---|---|---|
| CN | 101 875 716 | 3/2010 |
| CN | 101 875 717 | 3/2010 |

(Continued)

OTHER PUBLICATIONS

English Machine Translation of JP2006077171A.
International Search RepoOrt corresponding to PCT/EP2011/003952, dated Jun. 12, 2011.

*Primary Examiner* — Douglas McGinty
(74) *Attorney, Agent, or Firm* — Millen, White, Zelano, Branigan, P.C.

(57) ABSTRACT

The invention relates to novel polymers containing repeating units based on benzo[2,1,3]thiadiazole-5,6-dicarboxylic acid bis-ester, monomers and methods for their preparation, their use as semiconductors in organic electronic (OE) devices, especially in organic photovoltaic (OPV) devices, and to OE and OPV devices comprising these polymers.

17 Claims, No Drawings

(56) References Cited

U.S. PATENT DOCUMENTS

| | | |
|---|---|---|
| 2010/0243352 A1 | 9/2010 | Watanabe et al. |
| 2010/0282533 A1 | 11/2010 | Sugiyama |
| 2010/0307594 A1* | 12/2010 | Zhu .................. B82Y 10/00 136/263 |
| 2011/0121273 A1* | 5/2011 | Jo ..................... B82Y 10/00 257/40 |
| 2011/0127512 A1 | 6/2011 | Goto et al. |
| 2011/0156018 A1 | 6/2011 | Moriwaki et al. |
| 2011/0178236 A1* | 7/2011 | Tierney .............. C08G 61/122 524/589 |
| 2012/0187385 A1* | 7/2012 | Pan .................... B82Y 10/00 257/40 |
| 2013/0032791 A1* | 2/2013 | Bazan ................ C07D 495/04 257/40 |
| 2013/0043434 A1* | 2/2013 | Tierney .............. C07D 495/04 252/500 |
| 2013/0090446 A1* | 4/2013 | Zhou ................. C08G 61/123 528/8 |
| 2014/0084220 A1* | 3/2014 | Inagaki ............. H01L 51/0036 252/511 |
| 2014/0166942 A1* | 6/2014 | Izawa ................ H01L 51/0036 252/511 |
| 2014/0231791 A1* | 8/2014 | Funyuu ................ C08G 61/12 257/40 |

FOREIGN PATENT DOCUMENTS

| | | |
|---|---|---|
| CN | 101 928 382 | 12/2010 |
| EP | 2248693 | 11/2010 |
| JP | 2004002703 A | 1/2004 |
| JP | 2006077171 A | 3/2006 |
| JP | 2010084131 A | 4/2010 |
| JP | 2010507233 A5 | 9/2010 |
| WO | WO2004092246 A1 | 10/2004 |
| WO | WO2008016067 A1 | 2/2008 |
| WO | WO2008093822 A1 | 8/2008 |
| WO | WO2009139339 A1 | 11/2009 |
| WO | WO2009151144 A1 | 12/2009 |
| WO | 2011 131280 A1 | 10/2011 |

* cited by examiner

CONJUGATED POLYMERS

FIELD OF THE INVENTION

The invention relates to novel polymers containing repeating units based on benzo[2,1,3]thiadiazole-5,6-dicarboxylic acid bis-ester, monomers and methods for their preparation, their use as semiconductors in organic electronic (OE) devices, especially in organic photovoltaic (OPV) devices, and to OE and OPV devices comprising these polymers.

BACKGROUND OF THE INVENTION

In recent years there has been growing interest in the use of conjugated, semiconducting polymers for electronic applications. One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies up to 8%.

The conjugated polymer serves as the main absorber of the solar energy, therefore a low band gap is a basic requirement of the ideal polymer design to absorb the maximum of the solar spectrum.

A commonly used strategy to narrow the band gap of conjugated polymers is to utilize an alternating copolymer consisting of both electron rich donor units and electron deficient acceptor units within the polymer backbone. An acceptor unit that is known in prior art and has shown good photovoltaic performances when used in copolymers is 2,1,3-benzothiadiazole (BTZ) (see J. Chen, Y. Cao, Acc. Chem. Res., 2009, 42 (11), 1709):

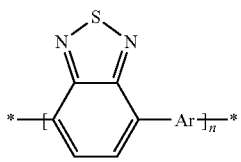

However, these polymers can have limited solubility in commonly used organic solvents, which can inhibit their suitability for device manufacturing methods based on solution processing). Therefore, the presence of additional solubilising functionality on the BTZ unit is desirable to expand the range of suitable processing solvents and their solid loading within these solvents.

More recently polymers containing 5,6-bis(octyloxy)-benzo[2,1,3]thiadiazole ((OR)$_2$BTZ) units have been prepared, like for example copolymers with fluorene having the following structure:

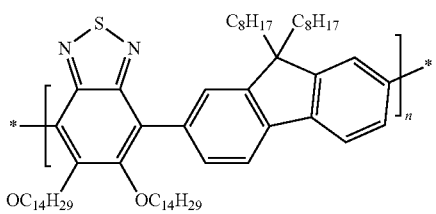

These polymers show improved solubility due to the flexible alkoxy side chains (see J. Bouffard, T. M. Swager, Macromolecules, 2008, 41(15), 5559).

Additionally, where the (OR)$_2$BTZ unit is flanked by two thiophene units, like in the copolymers shown below, the polymer retains the planar conformation of the back bone which is required to achieve the narrow band gaps and good charge carrier mobility required for OPV applications (see R. Qin, W. Li, C. Li, C. Du, C. Veit, H.-F. Schleiermacher, M. Andersson, Z. Bo, Z. Liu, O. Inganas, U. Wuerfel, F. Zhang, J. Am. Chem. Soc., 2009, 131, 14612; M. Helgesen, S. A. Gevorgyan, F. C. Krebs, R. A. J. Janssen, Chem. Mater., 2009, 21(19), 4669; W. Li, R. Qin, Y. Zhou, M. Andersson, F. Li, C. Zhang, B. Li, Z. Liu, Z. Bo, F. Zhang, Polymer, 2010, 51, 3031):

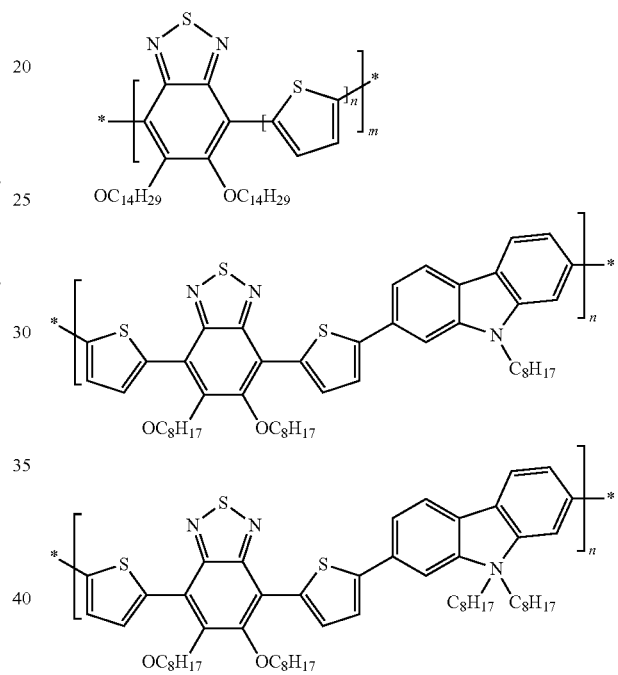

However, these polymers suffer from open circuit potentials (V$_{oc}$) in OPV bulk-heterojunction devices which are not attaining the theoretical maximum of ~1.15 V in a polymer/PCBM device (see J. C. Bijleveld, R. A. M. Verstrijden, M. M. Wienk, R. A. J. Janssen, Applied Physics Letters, 2010, 97, 073304).

Therefore, there is still a need for organic semiconducting (OSC) materials that are easy to synthesize, especially by methods suitable for mass production, show good structural organization and film-forming properties, exhibit good electronic properties, especially a high charge carrier mobility, good processability, especially a high solubility in organic solvents, and high stability in air. Especially for use in OPV cells, there is a need for OSC materials having a low bandgap, which enable improved light harvesting by the photoactive layer and can lead to higher cell efficiencies, and do not suffer from open circuit potentials (V$_{oc}$) in OPV bulk-heterojunction devices, or do so to a lower extent than polymers from prior art.

It was an aim of the present invention to provide compounds for use as organic semiconducting materials that do not have the drawbacks of prior art materials as described above, are easy to synthesize, especially by methods suitable for mass production, and do especially show good processability, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that these aims can be achieved by providing conjugated polymers containing BTZ units that are substituted in 5- and 6-position by ester groups to give benzo[2,1,3]thiadiazole-5,6-dicarboxylic acid bis-ester:

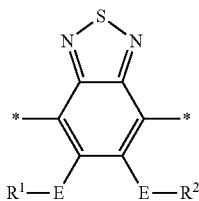

wherein E is CO—O or O—CO and $R^1$ and $R^2$ are carbyl groups like for example alkyl or aryl.

It was found that conjugated polymers based on this unit show good processability and high solubility in organic solvents, and are thus especially suitable for large scale production using solution processing methods. At the same time, they show a low bandgap, high charge carrier mobility and high oxidative stability and are promising materials for organic electronic OE devices, especially for OPV devices. Also, the addition of two electron withdrawing ester groups onto the BTZ acceptor unit deepens the HOMO level in order to achieve a higher open circuit potential ($V_{oc}$) in an OPV bulk-heterojunction device versus a device containing a polymer based upon BTZ or $(OR)_2BTZ$ while maintaining the same band-gap.

SUMMARY OF THE INVENTION

The invention relates to a conjugated polymer comprising one or more identical or different repeating units of formula I:

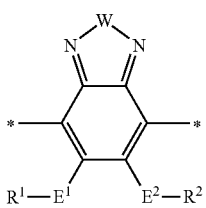

wherein an asterisk indicates a link to a neighboured group,
W is S, Se, O or $NR^x$,
$E^1$, $E^2$ are —O—C(O)— or —C(O)—O—,
$R^x$ is H or straight-chain, branched or cyclic alkyl with 1 to 30 C atoms, in which one or more non-adjacent C atoms are optionally replaced by —O—, —S—, —C(O)—, —C(O)—O—, —O—C(O)—, O—C(O)—O—, —CH=CH— or —C≡C— and in which one or more H atoms are optionally replaced by F, Cl, Br, I or CN,
$R^1$, $R^2$ are, each independently of one another, an optionally substituted $C_{1-40}$ carbyl or hydrocarbyl group.

The invention further relates to a conjugated polymer comprising one or more repeating units which contain a unit of formula I and/or contain one or more units (hereinafter also referred to as $Ar^1$, $Ar^2$ and $Ar^3$) selected from aryl and heteroaryl units that are optionally substituted, and wherein at least one of the repeating units in the polymer contains at least one unit of formula I.

Preferably, $R^1$ and $R^2$ in formula I are selected from straight-chain, branched or cyclic alkyl with 1 to 35 C atoms, in which one or more non-adjacent C atoms are optionally replaced by —O—, —S—, —C(O)—, —C(O)—O—, —O—C(O)—, —O—C(O)—O—, —$CR^0$=$CR^{00}$— or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups $R^3$, wherein
$R^0$ and $R^{00}$ are independently of each other H or optionally substituted $C_{1-40}$ carbyl or hydrocarbyl,
$R^3$ is on each occurrence identically or differently F, Br, Cl, —CN, —NC, —NCO, —NCS, —OCN, —SCN, —C(O)$NR^0R^{00}$, —C(O)$X^0$, —C(O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-,
P is a polymerisable or crosslinkable group,
Sp is a spacer group or a single bond, and
$X^0$ is halogen.

The conjugated polymers according to the present invention are preferably selected of formula II:

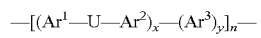

wherein
U is on each occurrence identically or differently a unit of formula I as described above and below,
$Ar^1$, $Ar^2$, $Ar^3$ are, on each occurrence identically or differently, and independently of each other, aryl or heteroaryl that is optionally substituted, preferably by one or more groups $R^3$ as defined above, and one or both of $Ar^1$ and $Ar^2$ may also denote a single bond,
$Y^1$ and $Y^2$ are independently of each other H, F, Cl or CN,
x is on each occurrence identically or differently 0, 1 or 2, wherein in at least one repeating unit, i.e. in at least one unit —[$(Ar^1—U—Ar^2)_x—(Ar^3)_y$]—, x is 1,
y is on each occurrence identically or differently 0, 1 or 2,
n is an integer >1.

The invention further relates to monomers containing a unit of formula I, which are suitable for the preparation of conjugated polymers as described above and below.

The invention further relates to a mixture or blend comprising one or more polymers according to the present invention and one or more additional compounds or polymers which are preferably selected from compounds and polymers having one or more of semiconducting, charge transport, hole or electron transport, hole or electron blocking, electrically conducting, photoconducting or light emitting properties.

The invention further relates to a formulation comprising one or more polymers, mixtures or or blends according to the present invention and optionally one or more solvents, preferably selected from organic solvents.

The invention further relates to the use of polymers, mixtures, blends and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more polymers, polymer blends of formulations according to the present invention.

The invention further relates to an optical, electrooptical or electronic component or device comprising one or more polymers, polymer blends, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

The monomers and polymers of the present invention are easy to synthesize and exhibit several advantageous properties, like a low bandgap, a high charge carrier mobility, a high solubility in organic solvents, a good processability for the device manufacture process, a high oxidative stability and a long lifetime in electronic devices.

In addition, they show the following advantageous properties:

i) Additional solubility can be introduced into the polymer by inclusion of the two solubilising ester groups or co-monomers containing multiple solubilising groups ii) The addition of two electron withdrawing ester groups onto the BTZ acceptor unit can modify the electronic energies (HOMO/LUMO levels) of the polymer, particularly a deepening of the HOMO level in order to achieve a higher open circuit potential ($V_{oc}$) in an OPV bulk-heterojunction device versus a device containing a polymer based upon BTZ.

iii) Additional fine-tuning of the electronic energies (HOMO/LUMO levels) by either further modification of the benzo[1,2-b;4,5-b']dithiophene core or co-polymerisation with appropriate co-monomer(s) should afford candidate materials for organic photovoltaic applications Above and below, the term "polymer" generally means a molecule of high relative molecular mass, the structure of which essentially comprises the multiple repetition of units derived, actually or conceptually, from molecules of low relative molecular mass (PAC, 1996, 68, 2291). The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having >1, preferably ≥5 repeating units, and an oligomer means a compound with >1 and <10, preferably <5, repeating units.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

The term "leaving group" means an atom or group (charged or uncharged) that becomes detached from an atom in what is considered to be the residual or main part of the molecule taking part in a specified reaction (see also PAC, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,3-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, chloroform, chlorobenzene or 1,2,4-trichlorobenzene. The degree of polymerization (n) means the number average degree of polymerization given as $n=M_n/M_U$, wherein $M_U$ is the molecular weight of the single repeating unit as described in J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and al koxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with 4 to 30 ring C atoms that may also comprise condensed rings and is optionally substituted with one or more groups L as defined above.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, pyridine, preferably 2- or 3-pyridine, pyrimidine, thiophene preferably 2-thiophene, selenophene, preferably 2-selenophene, thieno[3,2-b]thiophene, thiazole, thiadiazole, oxazole and oxadiazole, especially preferably thiophene-2-yl, 5-substituted thiophene-2-yl or pyridine-3-yl, all of which can be unsubstituted, mono- or polysubstituted with L as defined above.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e. where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, R is selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

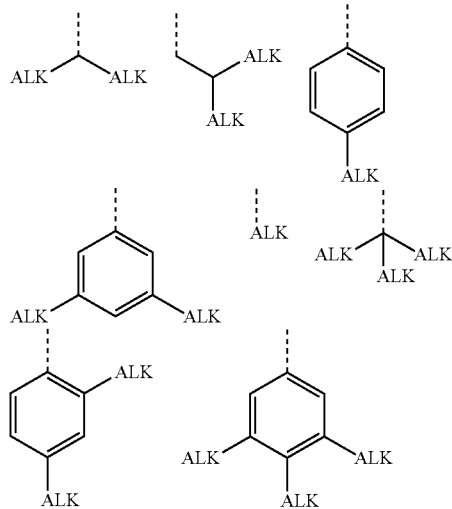

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—$CY^1$=$CY^2$— is preferably —CH=CH—, —CF=CF— or —CH=C(CN)—.

Halogen is F, Cl, Br or I, preferably F, Cl or Br.

—CO—, —C(=O)— and —C(O)— denote a carbonyl group, i.e.

The polymers may also be substituted with a polymerisable or crosslinkable reactive group, which is optionally protected during the process of forming the polymer. Particular preferred polymers of this type are those of formula I wherein $R^1$ denotes P-Sp. These polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or crosslinkable group P is selected from $CH_2$=$CW^1$—C(O)—O—, $CH_2$=$CW^1$—C(O)—,

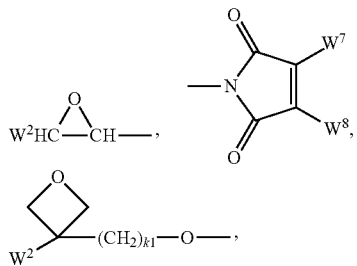

$CH_2$=$CW^2$—(O)$_{k1}$—, $CW^1$=CH—C(O)—(O)$_{k3}$—, $CW^1$=CH—C(O)—NH—, $CH_2$=$CW^1$—C(O)—NH—, $CH_3$—CH=CH—O—, ($CH_2$=CH)$_2$CH—OC(O)—, ($CH_2$=CH—($CH_2$)$_2$CH—O—C(O)—, ($CH_2$=CH)$_2$CH—O—, ($CH_2$=CH—($CH_2$)$_2$N—, ($CH_2$=CH—($CH_2$)$_2$N—C(O)—, HO—$CW^2W^3$—, HS—$CW^2W^3$—, $HW^2$N—, HO—$CW^2W^3$—NH—, $CH_2$=CH—(C(O)—O)$_{k1}$-Phe-(O)$_{k2}$—, $CH_2$=CH—(C(O))$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, $k_1$, $k_2$ and $k_3$ being independently of each other 0 or 1, $k_3$ preferably being 1, and $k_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—C(O)—O—, $CH_2$=C($CH_3$)—C(O)—O—, $CH_2$=CF—C(O)—O—, $CH_2$=CH—O—, ($CH_2$=CH)$_2$CH—O—C(O)—, ($CH_2$=CH)$_2$CH—O—,

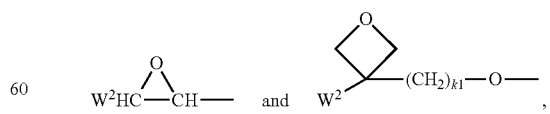

or protected derivatives thereof. Further preferred groups P are selected from the group consisting of vinyloxy, acrylate, methacrylate, fluoroacrylate, chloracrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, Macromol. Chem, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —C(O)—, —C(O)O—, —OC(O)—, —OC(O)—O—, —S—C(O)—, —C(O)—S—, —CH=CH— or —C≡C— in such a manner that O and/or S atoms are not linked directly to one another, X' is —O—, —S—, —C(O)—, —C(O)O—, —OC(O)—, —O—C(O)O—, —C(O)—$NR^0$—, —$NR^0$—C(O)—, —$NR^0$—C(O)—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—C(O)O—, —OC(O)—CH=CH— or a single bond, $R^0$ and $R^{00}$ are independently of each other H or alkyl with 1 to 12 C-atoms, and $Y^1$ and $Y^2$ are independently of each other H, F, Cl or CN. X' is preferably —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C— or a single bond, in particular —O—, —S—, —C≡C—, —$CY^1$=$CY^2$— or a single bond. In another preferred embodiment X' is a group that is able to form a conjugated system, such as —C≡C— or —$CY^1$=$CY^2$—, or a single bond.

Typical groups Sp' are, for example, —$(CH_2)_p$—, —$(CH_2CH_2O)_q$—$CH_2CH_2$—, —$CH_2CH_2$—S—$CH_2CH_2$— or —$CH_2CH_2$—NH—$CH_2CH_2$— or —$(SiR^0R^{00}$—O$)_p$—, with p being an integer from 2 to 12, q being an integer from 1 to 3 and $R^0$ and $R^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The polymers containing units of formula I, especially those of formula II, are preferably selected of formula IIa $$R^4—[(Ar^1—U—Ar^2)_x—(Ar^3)_y]_n—R^5 \quad \text{IIa}$$

wherein U, $Ar^{1-3}$, n, x and y have the meanings of formula I and II, and $R^3$ and $R^5$ have independently of each other one of the meanings of $R^3$, preferably F, Br or Cl, or denote H, —$CH_2Cl$, —CHO, —CH=$CH_2$, —SiR'R''R''', —SnR'R''R''', —BR'R'', —B(OR')(OR''), —$B(OH)_2$, or P-Sp, wherein P and Sp are as defined above, and R', R'' and R''' have independently of each other one of the meanings of $R^0$ defined above, and two of R', R'' and R''' may also form a ring together with the hetero atom to which they are attached.

In the polymers according to the the present invention, the total number of repeating units n is preferably ≥5, very preferably ≥10, most preferably ≥50, and preferably up to 500, very preferably up to 1,000, most preferably up to 2,000, including any combination of the aforementioned lower and upper limits of n.

The polymers of the present invention include homopolymers and copolymers, like statistical or random copolymers, alternating copolymers and block copolymers, as well as combinations thereof.

Block copolymers may for example comprise or consist of one or more blocks formed by units of formula I and one or more blocks formed by units $Ar^3$, wherein $Ar^3$ has one of the meanings of formula II or as described above and below.

Another aspect of the invention relates to monomers of formula Ia $$R^4—Ar^1—U—Ar^2—R^5 \quad \text{Ia}$$

wherein U, $Ar^1$, $Ar^2$, $R^4$ and $R^5$ have the meanings of formula II and IIa, or one of the preferred meanings as described above and below.

Especially preferred are monomers of formula Ia wherein $R^4$ and $R^5$ are, preferably independently of each other, selected from the group consisting of Cl, Br, I, O-tosylate, O-triflate, O-mesylate, O-nonaflate, —$SiMe_2F$, —$SiMeF_2$, —O—$SO_2Z^1$, —$B(OZ^2)_2$, —$CZ^3$=$C(Z^3)_2$, —C≡CH and —$Sn(Z^4)_3$, wherein $Z^{1-4}$ are selected from the group consisting of alkyl and aryl, each being optionally substituted, and two groups $Z^2$ may also form a cyclic group.

Preferably the repeating units of formula I, the monomers of formula Ia, and the polymers of formula II and IIa containing them, are selected from the following list of preferred embodiments:

W is S,
W is Se,
W is O,
W is $NR^x$,
$E^1$ is —O—C(O)— and $E^2$ is —C(O)—O, i.e. both ester groups are attached to the benzene ring in formula I via the carbonyl C-atom,
$E^1$ is —C(O)—O— and $E^2$ is O—C(O)—, i.e. both ester groups are attached to the benzene ring in formula I via the O-atom,
one of $Ar^1$ and $Ar^2$ is a single bond,
both $Ar^1$ and $Ar^2$ are a single bond,
both $Ar^1$ and $Ar^2$ are not a single bond,
$Ar^1$ and $Ar^2$, when being different from a single bond, are selected from the group consisting of thiophene-2,5-diyl, thiazole-2,5-diyl, selenophene-2,5-diyl, furan-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, or selenopheno[2,3-b]thiophene-2,5-diyl, all of which are unsubstituted, or mono- or polysubstituted, preferably with $R^3$ as defined above and below,
$Ar^3$ is selected from the group consisting of 1,4-phenylene, 2,3-dicyano-1,4-phenylene, 2,5-dicyano, 2,3-difluro-1,4-phenylene, 2,5-difluoro-1,4-phenylene, 2,3,5,6-tetrafluoro, 3,4-difluorothiophene-2,5-diyl, pyridine-2,5-diyl, pyrimidine-2,5-diyl, naphthalene-2,6-diyl, thiophene-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']di-thiophene-2, 6-diyl, 2,2-dithiophene, 2,2-diselenophene, dithieno[3,2-b:2',3'-d]silole-5,5-diyl, dithieno[3,2-b;2',3'-d]pyrrole-5,5-diyl, 4H-cyclopenta[2,1-b:3,4-b']dithiophene-2,6-diyl, carbazole-2,7-diyl, fluorene-2,7-diyl, indaceno[1,2-b:5,6-b]dithiophene-2,7-diyl, benzo[1",2":4,5;4",5":4',5']bis(silolo[3,2-b:3',2'-b]thiophene)-2,7-diyl, phenanthro[1,10,9,8-c,d,e,f,g]carbazole-2,7-diyl, benzo[2,1,3]thia-diazole-4,7-diyl, benzo[2,1,3]selenadiazole-4,7-diyl, benzo[2,1,3]oxa-diazole-4,7-diyl, 2H-benzotriazole-4,7-diyl, 3,4-difluorothiophene-2,5-diyl, quinoxaline-5,8-diyl, thieno[3,4-b]pyrazine-2,5-diyl, thieno[3,4-b]thiophene-4,6-diyl, thieno[3,4-b]thiophene-6,4-diyl, 3,6-di-thien-2-yl-pyrrolo[3,4-c]pyrrole-1,4-dione, or [1,3]thiazolo[5,4-d][1,3]thiazole-2,5-diyl, all of which are unsubstituted, or mono- or polysubstituted, preferably with $R^3$ as defined above and below, n is at least 5, preferably at least 10, very preferably at least 50, and up to 2,000, preferably up to 500.

$M_w$ is at least 5,000, preferably at least 8,000, very preferably at least 10,000, and preferably up to 300,000, very preferably up to 100,000, $R^1$ and $R^2$ are selected from the group consisting of primary alkyl or alkoxy with 1 to 30 C atoms, secondary alkyl or alkoxy with 3 to 30 C atoms, and tertiary alkyl or alkoxy with 4 to 30 C atoms, wherein in all these groups one or more H atoms are optionally replaced by F, $R^1$ and $R^2$ are selected from the group consisting of aryl, heteroaryl, aryloxy, heteroaryloxy, each of which is optionally alkylated or alkoxylated and has 4 to 30 ring atoms, $R^3$ is F, Cl, Br, I, CN, $R^6$, —C(O)—$R^6$, —C(O)—O—$R^6$, or —O—C(O)—$R^6$, wherein $R^6$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —CR$^0$=CR$^{00}$— or —C≡C— and in which one or more H atoms are optionally replaced by F, Cl, Br, I or CN, or $R^3$ is aryl, aryloxy, heteroaryl or heteroaryloxy having 4 to 30 ring atoms which is unsubstituted or which is substituted by one or more halogen atoms or by one or more groups $R^6$, —C(O)—$R^6$, —C(O)—O—$R^6$, or —O—C(O)—$R^6$ as defined above, $R^6$ is primary alkyl with 1 to 30 C atoms, very preferably with 1 to 15 C atoms, secondary alkyl with 3 to 30 C atoms, or tertiary alkyl with 4 to 30 C atoms, wherein in all these groups one or more H atoms are optionally replaced by F, $R^0$ and $R^{00}$ are selected from H or $C_1$-$C_{10}$-alkyl, $R^4$ and $R^5$ are selected from H, halogen, —CH$_2$Cl, —CHO, —CH=CH$_2$, —SiR'R"R''', —SnR'R"R''', —BR'R", —B(OR')(OR"), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, $R^4$ and $R^5$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z', —B(OZ$^2$)$_2$, —CZ$^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, very preferably from Br, $R^x$ is H, alkyl, alkoxy, alkylcarbonyl, alkylcarbonyloxy or alkoxycarbonyl with 1 to 30 C atoms, wherein one or more H atoms are optionally replaced by F.

Preferred polymers of formula II are selected from the group consisting of the following formulae:

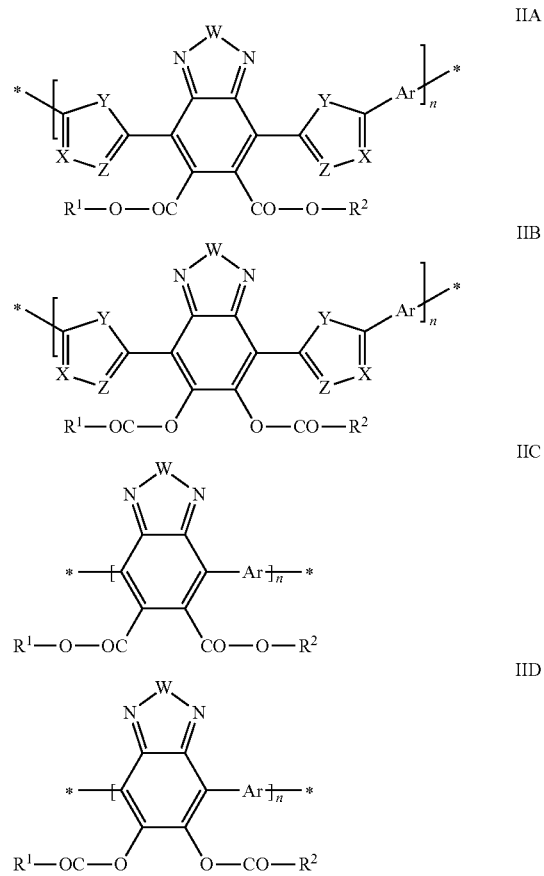

wherein Ar denotes a group of formula 1, 2 or 3

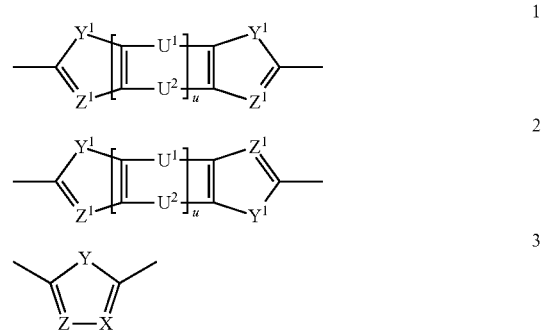

X is C($R^x$) or N,
Y is O, S, Se or N($R^x$),
Z is C($R^x$) or N,
$Y^1$ is O, S, Se, N($R^x$), or —CH=CH—,
Z' is C($R^x$) or N,
W and $R^x$ have the meanings of formula I or one of the preferred meanings given above and below,
$U^1$ and $U^2$ are each, independently of one another, —C($R^x$)=, —C($R^xR^y$)—, —S(i$R^xR^y$)—, —N($R^x$)—, —S—, —Se—, —O— or a single bond, wherein $U^1$ and $U^2$ are not both a single bond, $R^y$ has one of the meanings given for $R^x$,
u is 0 or 1,
n has the meaning of formula II or one of the preferred meanings given above and below.

Especially preferred are polymers of formulae IIA-IID wherein W is S. Further preferred are polymers of formulae IIA-IID, wherein X and Z are $C(R^x)$ and Y is S or Se, most preferably S.

Further preferred are polymers of formulae IIA-IID, wherein Ar is a group of formula 1 or 2 in which u is 1, in particular those selected from the following groups:
  the group consisting of polymers wherein Z is $C(R^x)$ and Y is S or Se, very preferably S, and/or wherein W is S,
  the group consisting of polymers wherein $U^1$ and $U^2$ are —$C(R^x)$=,
  the group consisting of polymers wherein one of $U^1$ and $U^2$ is a single bond and the other is —$C(R^xR^y)$—, —$S(iR^xR^y)$— or —$N(R^x)$—,
  the group consisting of polymers wherein Ar is of formula 1, $U^1$ is a single bond and $U^2$ is —$C(R^xR^y)$—, —$S(iR^xR^y)$— or —$N(R^x)$—, very preferably wherein X, Z and Z' denote $C(R^x)$ and Y and Y' denote S or Se, most preferably S,
  the group consisting of polymers wherein Ar is formula 1, Y' is —CH=CH— and Z' is $C(R^x)$, and preferably X and Z are $C(R^x)$ and Y is S or Se, most preferably S,
  the group consisting of polymers wherein Ar is of formula 1, Y' is —CH=CH—, Z' is $C(R^x)$, $U^1$ is a single bond, and $U^2$ is —$C(R^xR^y)$—, —$S(iR^xR^y)$— or —$N(R^x)$—, and preferably wherein X and Z are $C(R^x)$ and Y is S or Se, most preferably S,
  the group consisting of polymers wherein Ar is of formula 2, $U^1$ and $U^2$ are —$C(R^x)$=, and preferably wherein X, Z and Z' denote $C(R^x)$ and Y and Y' denote S or Se, most preferably S.

Further preferred are polymers of formulae IIA-IID, wherein Ar is a group of formula 1 or 2 in which u is 0, very preferably wherein X, Z and Z' denote $C(R^x)$ and Y and Y' denote S or Se, most preferably S.

Further preferred are polymers of formulae IIA-IID, preferably those of formula IIC or IID, wherein Ar is a group of formula 3, X and Z are $C(R^x)$ and Y is S or Se, very preferably S.

Very preferred polymers of formulae II and IIA-IID are selected from the group consisting of the following formulae:

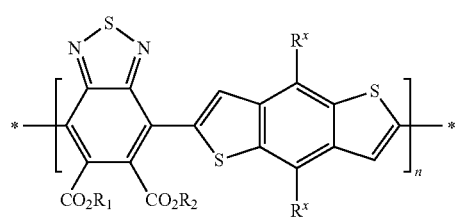

II1

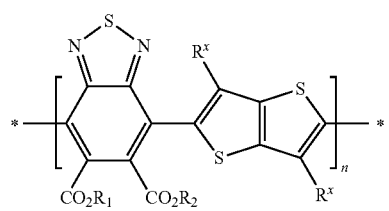

II2

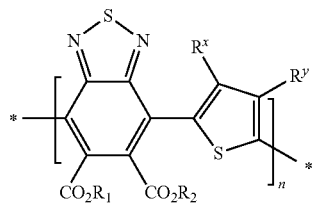

II3

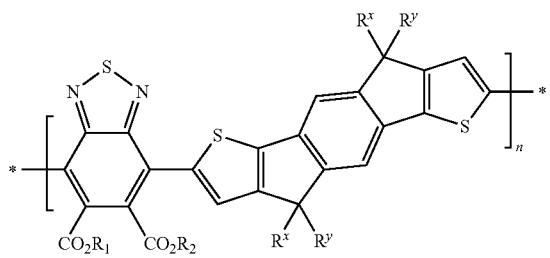

II4

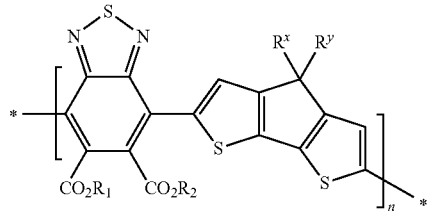

II5

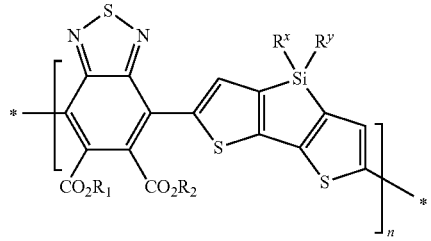

II6

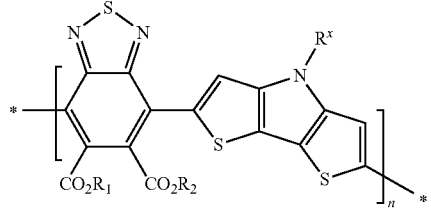

II7

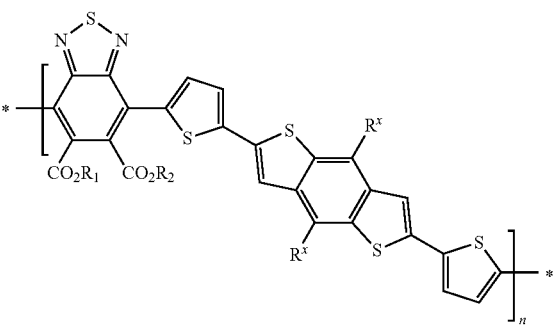

II8

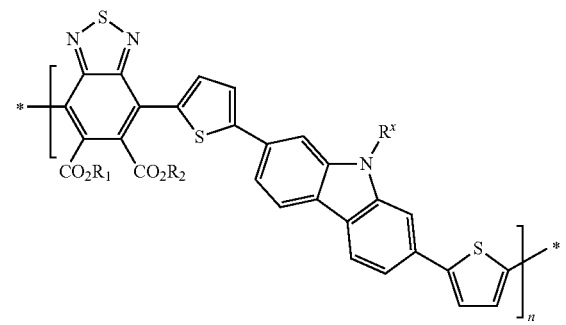

II9

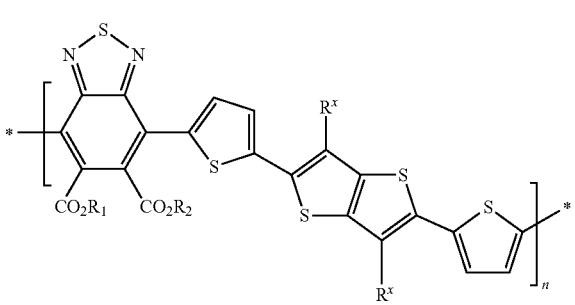

II10

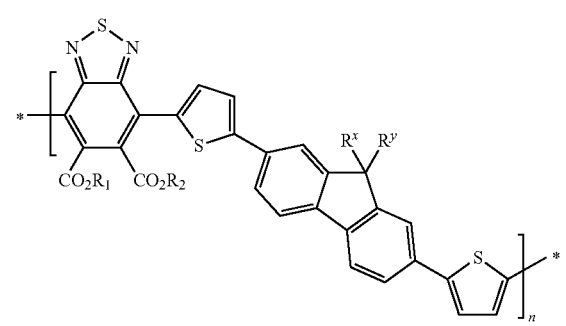

II11

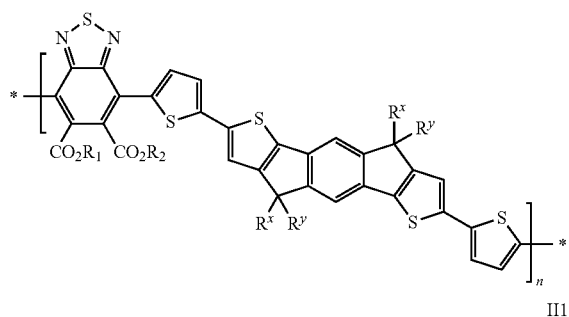

II12

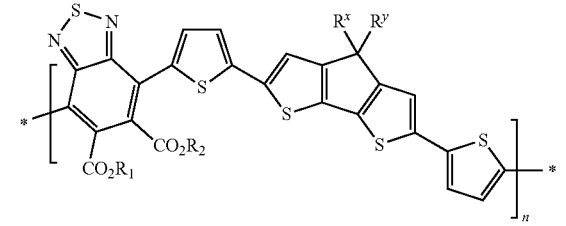

II13

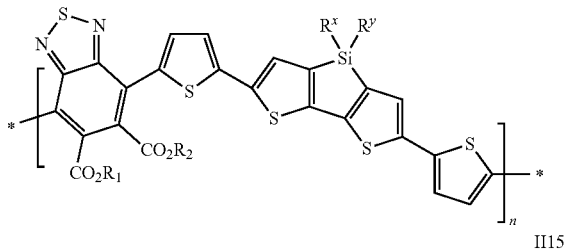

II14

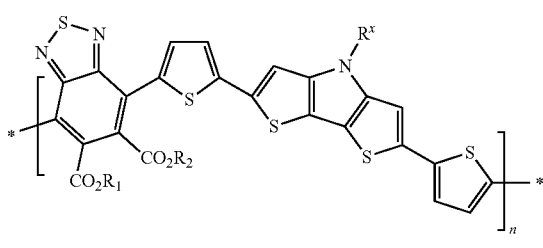

II15 wherein $R^1$, $R^2$, $R^x$, $R^y$ and n have the meanings as given in formula I, II and IIA, or one of the preferred meanings given above and below.

Preferred polymers of formula IIa are selected of the formula $$R^4\text{-chain-}R^5$$

wherein "chain" is a polymer chain selected from above formulae IIA-IID and II1-15, and $R^4$ and $R^5$ have one of the meanings given in formula IIa or one of the preferred meanings given above and below.

The polymers of the present invention can be synthesized according to or in analogy to methods that are known to the skilled person and are described in the literature. Other methods of preparation can be taken from the examples. For example, they can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The monomers which are polymerised to form the repeat units of the polymers can be prepared according to methods which are known to the person skilled in the art.

Preferably the polymers are prepared from monomers of formula Ia or its preferred embodiments as described above and below.

Another aspect of the invention is a process for preparing a polymer by coupling one or more identical or different monomeric units of formula I or monomers of formula Ia with each other and/or with one or more comonomers in a polymerisation reaction, preferably in an aryl-aryl coupling reaction.

Suitable and preferred comonomers are those of the formula $$R^4\text{—Ar}^3\text{—}R^5$$

wherein $R^4$ and $R^5$ have one of the meanings of formula IIa or one of the preferred meanings given above and below, and $Ar^3$ has one of the meanings of formula IIa or of Ar in formula IIa, or one of the preferred meanings given above and below.

Preferred methods for polymerisation are those leading to C—C-coupling or C—N-coupling, like Suzuki polymerisation, as described for example in WO 00/53656, Yamamoto polymerisation, as described in for example in T. Yamamoto et al., Progress in Polymer Science 1993, 17, 1153-1205 or in WO 2004/022626 A1, and Stille coupling. For example, when synthesizing a linear polymer by Yamamoto polymerisation, monomers as described above having two reactive halide groups $R^2$ and $R^3$ is preferably used. When synthesizing a linear polymer by Suzuki polymerisation, preferably a monomer as described above is used wherein at least one reactive group $R^2$ or $R^3$ is a boronic acid or boronic acid derivative group.

Suzuki polymerisation may be used to prepare homopolymers as well as statistical, alternating and block random copolymers. Statistical or block copolymers can be prepared for example from the above monomers of formula Ia wherein one of the reactive groups $R^2$ and $R^3$ is halogen and the other reactive group is a boronic acid or boronic acid derivative group.

The synthesis of statistical, alternating and block copolymers is described in detail for example in WO 03/048225 A2 or WO 2005/014688 A2.

Suzuki polymerisation employs a Pd(O) complex or a Pd(II) salt. Preferred Pd(O) complexes are those bearing at least one phosphine ligand such as $Pd(Ph_3P)_4$. Another preferred phosphine ligand is tris(ortho-tolyl)phosphine, i.e. $Pd(o-Tol)_4$. Preferred Pd(II) salts include palladium acetate, i.e. $Pd(OAc)_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O—$SO_2Z^1$ can be used wherein $Z^1$ is as described above. Particular examples of such leaving groups are tosylate, mesylate and triflate.

Especially suitable and preferred synthesis methods of the repeating units and monomers of formula I and Ia, and their homo- and co-polymers of formula II and IIa, are illustrated in the synthesis schemes shown hereinafter, wherein R, $Ar^1$, $Ar^2$ and $Ar^3$ are as defined in formula I and II.

A synthesis scheme for the preparation of 4,7-dibromo-benzo[2,1,3]thiadiazole-5,6-dicarboxylic acid bis-ester and 4,7-bis-(5-bromo-thiophen-2-yl)-benzo[2,1,3]thiadiazole-5,6-dicarboxylic acid bis-ester is shown in Scheme 1 (see C. Burmester, R. Faust, *Synthesis*, 2008, 8, 1179, and WO2010031479 A1).

Scheme 1

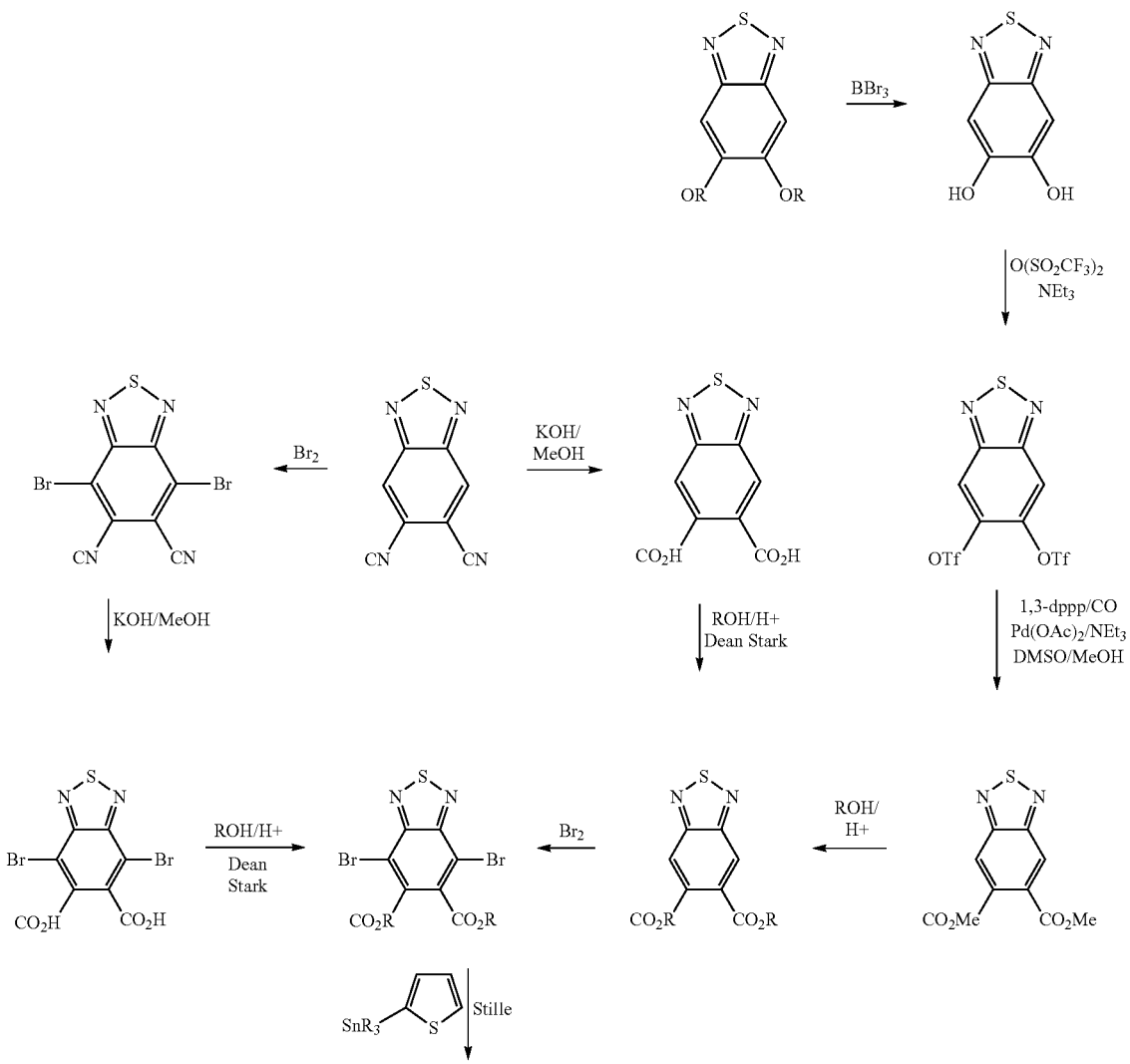

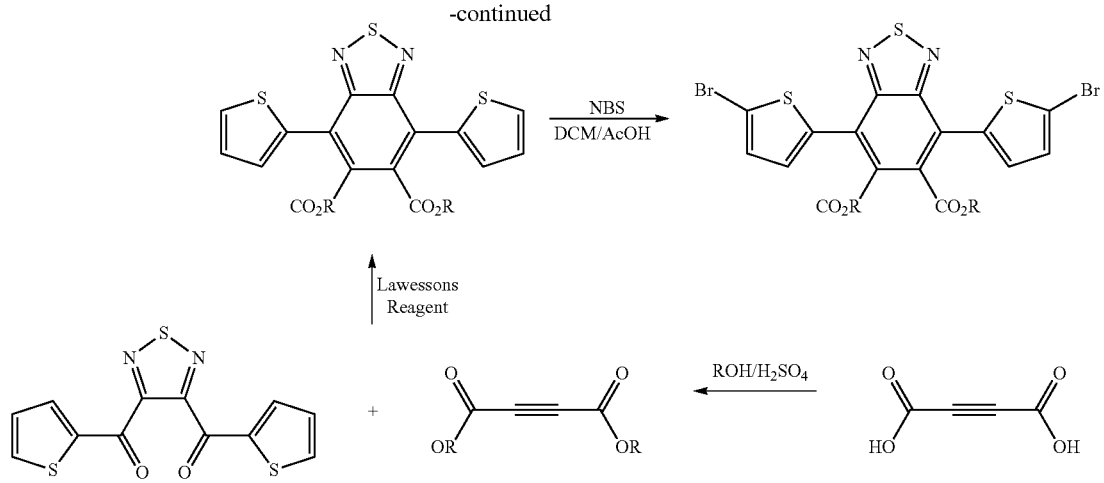
Synthesis schemes for the co-polymerisation of 4,7-dibromo-benzo[2,1,3]thiadiazole-5,6-dicarboxylic acid bis-ester and 4,7-bis-(5-bromo-thiophen-2-yl)-benzo[2,1,3]thiadiazole-5,6-dicarboxylic acid bis-ester are shown in Scheme 2 (alternating copolymers) and Scheme 3 (random copolymer).
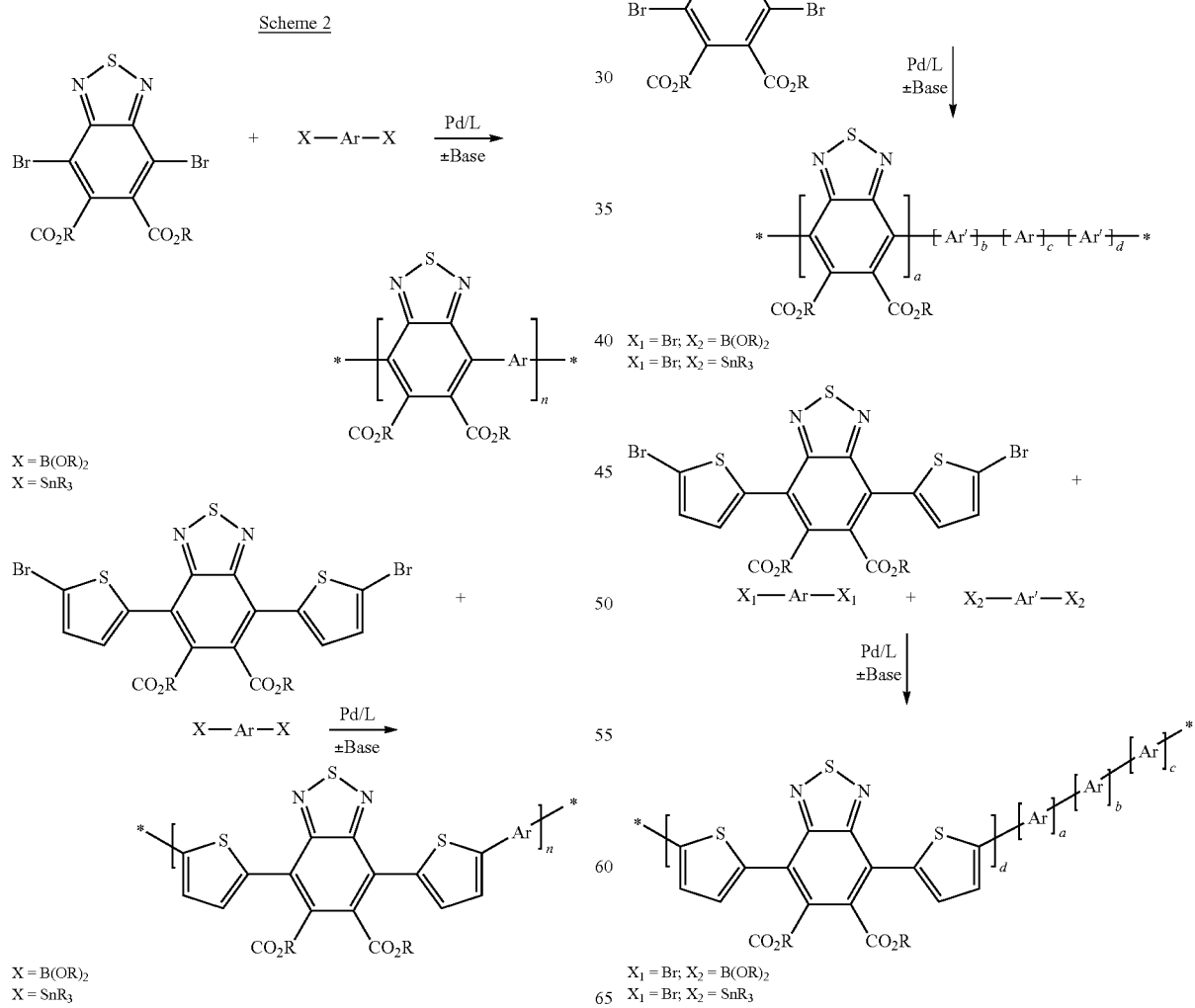

The novel methods of preparing monomers and polymers as described above and below are another aspect of the invention.

The polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986".

Such a procedure may lead to a blend of 'non' solvents that will dissolve both the polymers of the present invention, although it is desirable to have at least one true solvent in a blend.

The polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents methoned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers or formulations according to the present invention can additionally comprise one or more further components or additives selected for for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers according to the present invention are useful as charge transport, semiconducting, electrically conducting, photoconducting or light mitting materials in optical, electrooptical, electronic, electroluminescent or photoluminescent components or devices. In these devices, the polymers of the present invention are typically applied as thin layers or films.

Thus, the present invention also provides the use of the semiconducting polymer, polymer blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide or cadmium selenide, or an organic material such as a fullerene derivate, for example (6,6)-phenyl C61-butyric acid methyl ester, also known as "PCBM" or "PC$_{61}$BM", as disclosed for example in G. Yu, J. Gao, J. C. Hummelen, F. Wudl, A. J. Heeger, Science 1995, Vol. 270, p. 1789 ff and having the structure shown below, or an structural analogous compound with e.g. a C$_{71}$ fullerene group (PC$_{71}$BM), or a polymer (see for example Coakley, K. M. and McGehee, M. D. *Chem. Mater.* 2004, 16, 4533).

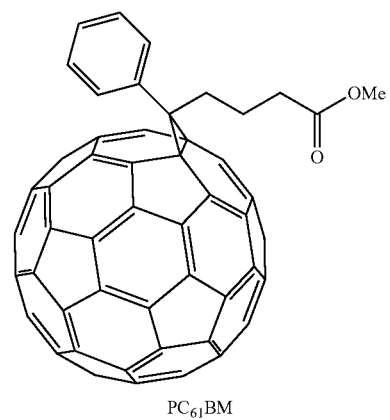

PC$_{61}$BM

A preferred material of this type is a blend or mixture of a polymer according to the present invention with a C$_{60}$ or C$_{70}$ fullerene or modified C$_{60}$ fullerene like PC$_{61}$BM or PC$_{71}$BM. Preferably the ratio polymer:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently OPV device performance.

The OPV device can for example be of any type known from the literature [see e.g. Waldauf et al., Appl. Phys. Lett. 89, 233517 (2006)].

A first preferred OPV device according to the invention comprises:
  a low work function electrode (11) (for example a metal, such as aluminum), and a high work function electrode (12) (for example ITO), one of which is transparent,
  a layer (13) (also referred to as "active layer") comprising a hole transporting material and an electron transporting material, preferably selected from OSC materials, situated between the electrodes (11,12); the active layer can exist for example as a bilayer or two distinct layers or blend or mixture of p-type and n-type semiconductor, forming a bulk heterjunction (BHJ) (see for example Coakley, K. M. and McGehee, M. D. *Chem. Mater.* 2004, 16, 4533), an optional conducting polymer layer (14), for example comprising a blend of PEDOT:PSS (poly(3,4-ethylenedioxythiophene):poly(styrenesulfonate)), situated between the active layer (13) and the high work function electrode (12), to modify the work function of the high work function electrode to provide an ohmic contact for holes, an optional coating (15) (for example of LiF) on the side of the low workfunction electrode (11) facing the active layer (13), to provide an ohmic contact for electrons.

A second preferred OPV device according to the invention is an inverted OPV device and comprises:

a low work function electrode (21) (for example a metal, such as gold), and a high work function electrode (22) (for example ITO), one of which is transparent, a layer (23) (also referred to as "active layer") comprising a hole transporting material and an electron transporting material, preferably selected from OSC materials, situated between the electrodes (21,22); the active layer can exist for example as a bilayer or two distinct layers or blend or mixture of p-type and n-type semiconductor, forming a BHJ, an optional conducting polymer layer (24), for example comprising a blend of PEDOT:PSS, situated between the active layer (23) and the low work function electrode (21) to provide an ohmic contact for electrons, an optional coating (25) (for example of $TiO_x$) on the side of the high workfunction electrode (22) facing the active layer (23), to provide an ohmic contact for holes.

In the OPV devices of the present invent invention the p-type and n-type semiconductor materials are preferably selected from the materials, like the polymer/fullerene systems, as described above. If the bilayer is a blend an optional annealing step may be necessary to optimize device performance.

The compound, formulation and layer of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processability of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:

a source electrode,
a drain electrode,
a gate electrode,
a semiconducting layer,
one or more gate insulator layers,
optionally a substrate.

wherein the semiconductor layer preferably comprises a polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass).

Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., Science, 279, 1998, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cr^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention any also be suitable for use in organic plasmon-emitting diodes (OPEDs), as described for example in Koller et al., Nature Photonics 2008 (published online Sep. 28, 2008).

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention will now be described in more detail by reference to the following examples, which are illustrative only and do not limit the scope of the invention.

Example 1

But-2-ynedioic acid bis-(2-ethyl-hexyl) ester

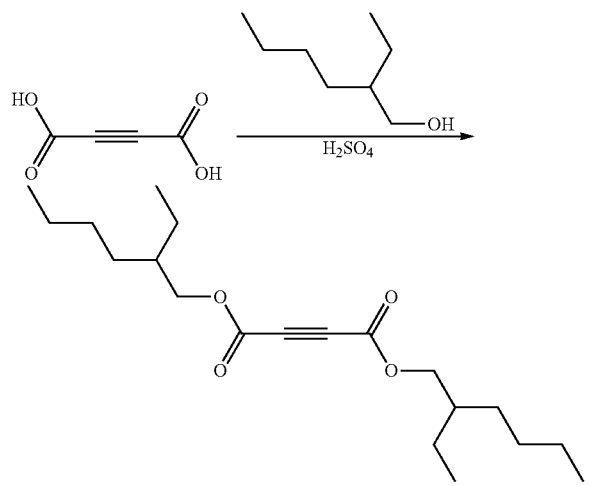

A mixture of acetylenedicarboxylic acid (25.0 g, 219 mmol), ethylhexanol (103 cm$^3$, 660 mmol), anhydrous toluene (100 cm$^3$) and sulfuric acid (10 cm$^3$) is heated at reflux under Dean-Stark conditions for 17 hours. The mixture is allowed to cool, brine (200 cm$^3$) added and the product extracted with ether (2×250 cm$^3$). The combined organic extracts dried over anhydrous magnesium sulfate, filtered and the solvent removed in vacuo to give a brown oil. The residue is distilled under vacuum (144° C., 0.07 mBar) to give but-2-ynedioic acid bis-(2-ethyl-hexyl) ester as a pale yellow oil (31.9 g, 36%). $^1$H NMR (300 MHz, CDCl$_3$) 0.85-0.95 (12H, m, CH$_3$), 1.23-1.41 (16H, m, CH$_2$), 1.57-1.70 (2H, m, CH), 4.11-4.21 (4H, m, OCH$_2$); $^{13}$C NMR (300 MHz, CDCl$_3$) 10.9, 14.0, 22.9, 23.5, 28.8, 30.1, 38.6, 69.2, 74.7, 152.1.

4,7-Di-thiophen-2-yl-benzo[2,1,3]thiadiazole-5,6-dicarboxylic acid bis-(2-ethyl-hexyl)ester

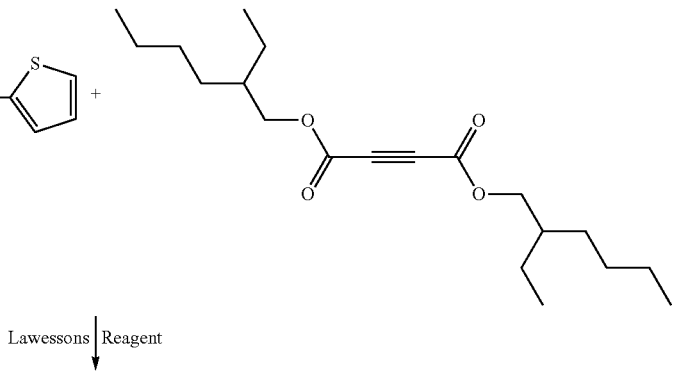

Lawessons Reagent

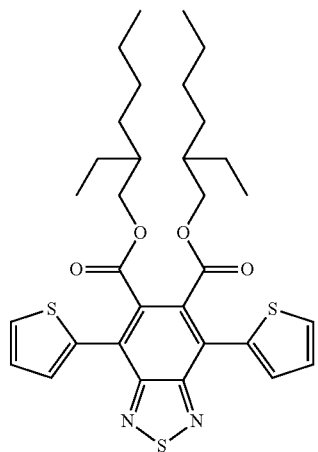

A mixture of [4-(thiophene-2-carbonyl)-[2,1,3]thiadiazol-3-yl]-thiophen-2-yl-methanone (1.7 g, 6 mmol), anhydrous toluene (70 cm³) and Lawesson's reagent (3.8 g, 9.5 mmol) is stirred at room temperature for 2 hours. But-2-ynedioic acid bis-(2-ethyl-hexyl) ester (3.4 g, 10 mmol) is then added and the reaction mixture heated at reflux for 17 hours. Acetone (50 cm³) is added, the mixture pre-absorbed onto silica and purified by column chromatography (40-60 petrol: ethyl acetate; 1:0 to 3:1) to give 4,7-di-thiophen-2-yl-benzo[2,1,3]thiadiazole-5,6-dicarboxylic acid bis-(2-ethyl-hexyl) ester as a yellow/green oil (380 mg, 11%). ¹H NMR (300 MHz, CDCl₃) 0.71-0.99 (12H, m, CH₃), 1.03-1.47 (16H, m, CH₂), 1.50-1.75 (2H, m, CH), 3.94-4.15 (4H, m, OCH₂), 7.18 (2H, dd, ArH, J 3.6, 5.0), 7.41 (2H, dd, ArH, J 1.2, 3.6), 7.58 (2H, dd, ArH, J 1.2, 5.0); ¹³C NMR (300 MHz, CDCl₃) 10.9, 14.1, 23.0, 23.3, 28.9, 30.0, 38.4, 68.9, 126.0, 127.3, 128.7, 129.6, 132.8, 135.3, 153.7, 167.9.

4,7-Bis-(5-bromo-thiophen-2-yl)-benzo[2,1,3]thiadiazole-5,6-dicarboxylic acid bis-(2-ethyl-hexyl) ester

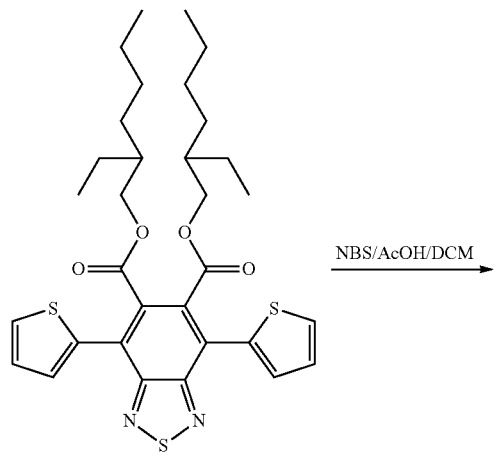

NBS/AcOH/DCM

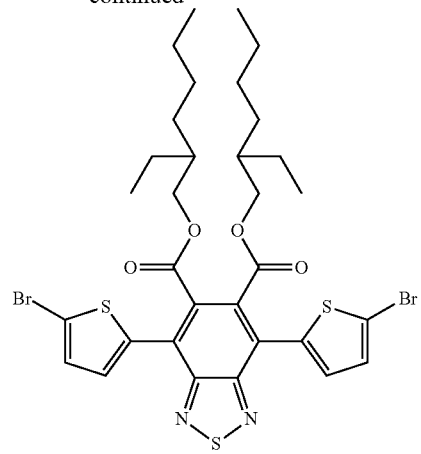

To a solution of 4,7-di-thiophen-2-yl-benzo[2,1,3]thiadiazole-5,6-dicarboxylic acid bis-(2-ethyl-hexyl) ester (360 mg, 0.59 mmol) in dichloromethane (50 cm³) and glacial acetic acid (50 cm³) in the dark is added N-bromosuccinimide (210 mg, 1.18 mmol) and the mixture is stirred at room temperature for 17 hours. Further N-bromosuccinimide (160 mg, 0.90 mmol) is added and the mixture stirred at room temperature for 4 hours. Water (250 cm³) added to the mixture and the product extracted with dichloromethane (2×200 cm³). The combined organic extracts are dried over anhydrous magnesium sulfate, filtered, and the solvent removed in vacuo to give a yellow oil. The crude material columned (40-60 petrol:ethyl acetate; 1:0 to 3:1) to give 4,7-bis-(5-bromo-thiophen-2-yl)-benzo[2,1,3]thiadiazole-5,6-dicarboxylic acid bis-(2-ethyl-hexyl) ester as an orange/yellow oil (140 mg, 31%). ¹H NMR (300 MHz, CDCl₃) 0.78-0.92 (12H, m, CH₃), 1.13-1.33 (16H, m, CH₂), 1.39-1.50 (2H, m, CH), 4.01-4.13 (4H, m, OCH₂), 7.12 (2H, d, ArH, J 3.9), 7.15 (2H, d, ArH, J 3.9); ¹³C NMR (300 MHz, CDCl₃) 10.9, 14.1, 23.0, 23.4, 28.9, 30.1, 38.5, 69.1, 116.4, 125.2, 129.9, 130.1, 132.7, 136.8, 153.2, 167.6.

Poly{4,7-benzo[2,1,3]thiadiazole-5,6-dicarboxylic acid bis-(2-ethyl-hexyl) ester}-alt-{5,5(2,6-bis[2-thienyl]-4,8-dioctylbenzo[1,2-b:4,5-b]dithiophene)}

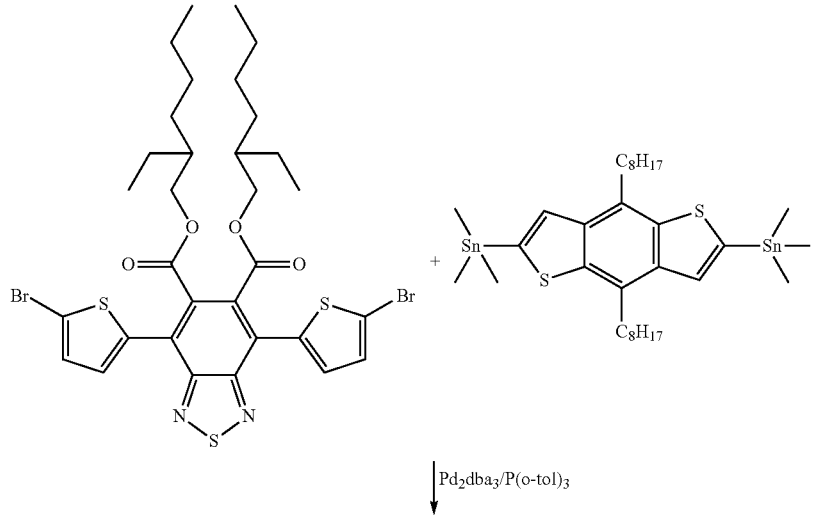

Pd₂dba₃/P(o-tol)₃

-continued

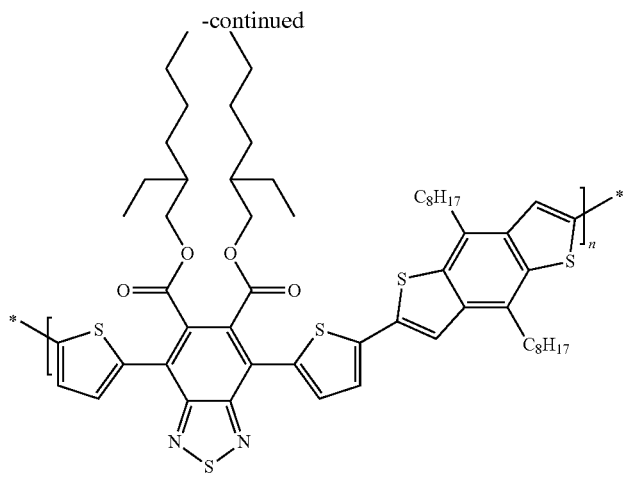

A mixture of 4,8-dioctyl-2,6-bis-trimethylstannanyl-benzo[1,2-b;4,5-b']dithiophene (133.2 mg, 0.18 mmol), 4,7-bis-(5-bromo-thiophen-2-yl)-benzo[2,1,3]thiadiazole-5,6-dicarboxylic acid bis-(2-ethyl-hexyl) ester (138.7 mg, 0.18 mmol), tris(dibenzyl-ideneacetone)dipalladium(O) (1.6 mg, 0.002 mmol), tri(o-tolyl)phosphine (2.2 mg, 0.007 mmol) is subjected to three successive cycles of vacuum followed by refilling with nitrogen. To this is added degassed anhydrous toluene (5 cm$^3$) and degassed anhydrous N,N-dimethylformamide (1 cm$^3$). The mixture is then heated at 110° C. for 17 hours. The mixture is allowed to cool and poured into stirring acidified methanol (10% hydrochloric acid, 50 cm$^3$) and the precipitate stirred for 30 minutes. The solid is then collected by filtration, washed with methanol (100 cm$^3$) to give a black solid. The crude polymer is washed via Soxhlet extraction with acetone, 40-60 petrol and chloroform. The chloroform extract is concentrated in vacuo and precipitated into stirred methanol (50 cm$^3$). The polymer collected by filtration and dried under vacuum to give poly{4,7-benzo[2,1,3]thiadiazole-5,6-dicarboxylic acid bis-(2-ethyl-hexyl) ester}-alt-{5,5(2,6-bis[2-thienyl]-4,8-dioctylbenzo[1,2-b:4,5-b']dithiophene)} as a black solid (100 mg, 54%). GPC (chlorobenzene) $M_n$: 16,600, $M_w$: 28,700, pd: 1.73.

Photovoltaic Cell Fabrication and Measurement

Organic photovoltaic (OPV) devices were fabricated on ITO-glass substrates (13 Ω/sq.) purchased from LUMTEC Corporation. Substrates were cleaned using common solvents (acetone, iso-propanol, deionized-water) in an ultrasonic bath prior to a conventional photolithography process that was carried out to define the bottom electrodes (anodes). A conducting polymer poly(ethylene dioxythiophene) doped with poly(styrene sulfonic acid) [Clevios VPAI 4083 (H. C. Starck)] was mixed in a 1:1 ratio with deionized-water. This solution was sonicated for 20 minutes to ensure proper mixing and filtered using a 0.2 μm filter before spin-coating to achieve a thickness of 20 nm. Substrates were exposed to ozone prior to the spin-coating process to ensure good wetting properties. Films were then annealed at 130° C. for 30 minutes in a nitrogen atmosphere where they were kept for the remainder of the process. Active materials solutions were prepared at the concentration and components ratio stated in the examples and stirred overnight. Thin films were either spin-coated or blade-coated in a nitrogen atmosphere to achieve active layer thicknesses between 100 and 250 nm as measured using a profilometer. A short drying period followed to ensure removal of any residual solvent. Typically, spin-coated films were dried at 23° C. for 10 minutes and blade-coated films were dried at 70° C. for 2 minutes on a hotplate. For the last step of the device fabrication, Ca (30 nm)/Al (200 nm) cathodes were thermally evaporated through a shadow mask to define the cells. Samples were measured at 23° C. under the irradiation of 1 Sun using a Solar Simulator (Newport Ltd, Model 91160) as the light source and using a calibrated Si-cell as the reference.

OPV device characteristics for blends of polymer examples (1)-(5) with $PC_{61}BM$ under irradiation of 1 Sun are shown in table 1.

Example 1

20 mg/ml concentration, 1:2 ratio OPV:PCBM[60]

Example 2

30 mg/ml concentration, 1:2 ratio OPV:PCBM[60]

Example 3

40 mg/ml concentration, 1:2 ratio OPV:PCBM[60]

Example 4

30 mg/ml concentration, 1:1 ratio OPV:PCBM[60]

Example 5

30 mg/ml concentration, 1:3 ratio OPV:PCBM[60]

TABLE 1

| Photovoltaic cell characteristics | | | | |
|---|---|---|---|---|
| Example | η (%) | FF | $V_{oc}$ (mV) | $J_{sc}$ (mA/cm$^2$) |
| (1) | 0.33 | 29 | 627 | −1.77 |
| (2) | 0.33 | 34 | 774 | −1.25 |
| (3) | 0.39 | 33 | 769 | −1.54 |
| (4) | 0.33 | 29 | 863 | −1.35 |
| (5) | 0.26 | 32 | 750 | −1.06 |

The invention claimed is:
1. A polymer according selected from the following formulae:

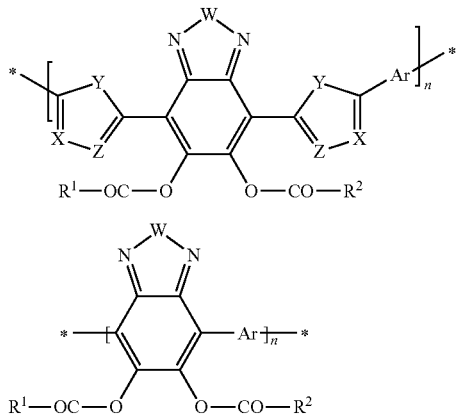

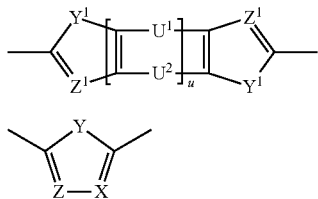

wherein Ar denotes a group of formula 2 or 3

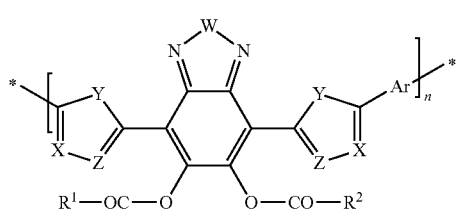

X is $C(R^x)$ or N,
Y is O, S, Se or $N(R^x)$,
Z is $C(R^x)$ or N,
$Y^1$ is O, S, Se, $N(R^x)$, or —CH=CH—,
$Z^1$ is $C(R^x)$ or N,
W is S, Se, O or $NR^x$,
$R^1$, $R^2$ are, each independently of one another, an optionally substituted $C_{1\text{-}40}$ carbyl or hydrocarbyl group,
$U^1$ and $U^2$ are each, independently of one another, —$C(R^x)$=, —$C(R^xR^y)$—, —$Si(R^xR^y)$—, —$N(R^x)$—, —S—, —Se—, —O— or a single bond, wherein $U^1$ and $U^2$ are not both a single bond,
$R^x$ and $R^y$ are each H or straight-chain, branched or cyclic alkyl with 1 to 30 C atoms, in which one or more non-adjacent C atoms are each optionally replaced by —O—, —S—, —C(O)—, —C(O)—O—, —O—C(O)—, O—C(O)—O—, —CH=CH— or —C≡C— and in which one or more H atoms are each optionally replaced by F, Cl, Br, I or CN,
u is 0 or 1, and
n is an integer >1.

2. A polymer according selected from the following formula:

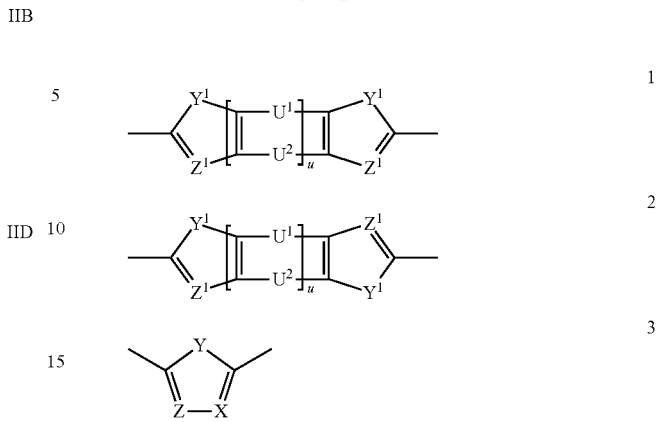

wherein Ar denotes a group of formula 1, 2 or 3

X is $C(R^x)$ or N,
Y is O, S, Se or $N(R^x)$,
Z is $C(R^x)$ or N,
$Y^1$ is O, S, Se, $N(R^x)$, or —CH=CH—,
$Z^1$ is $C(R^x)$ or N,
W is S, Se, O or $NR^x$,
$R^1$, $R^2$ are, each independently of one another, an optionally substituted $C_{1\text{-}40}$ carbyl or hydrocarbyl group,
$U^1$ and $U^2$ are each, independently of one another, —$C(R^x)$=, —$C(R^xR^y)$—, —$Si(R^xR^y)$—, —$N(R^x)$—, —S—, —Se—, —O— or a single bond, wherein $U^1$ and $U^2$ are not both a single bond,
$R^x$ and $R^y$ are each H or straight-chain, branched or cyclic alkyl with 1 to 30 C atoms, in which one or more non-adjacent C atoms are each optionally replaced by —O—, —S—, —C(O)—, —C(O)—O—, —O—C(O)—, O—C(O)—O—, —CH=CH— or —C≡C— and in which one or more H atoms are each optionally replaced by F, Cl, Br, I or CN,
u is 0 or 1, and
n is an integer >1.

3. A polymer according selected from the following formulae:

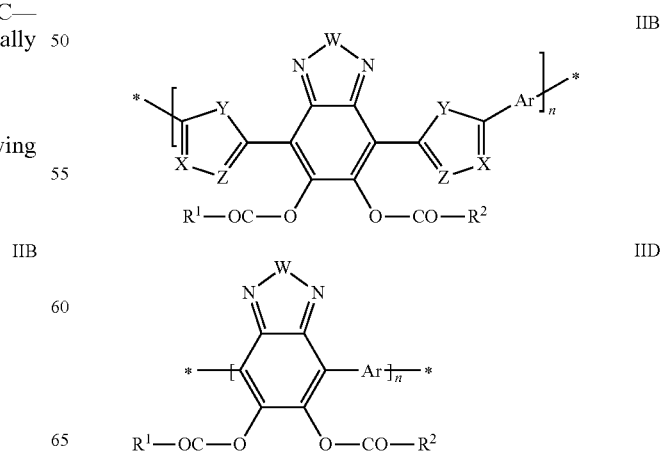

wherein Ar denotes a group of formula 1

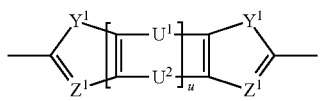

X is $C(R^x)$ or N,
Y is O, S, Se or $N(R^x)$,
Z is $C(R^x)$ or N,
$Y^1$ is O, S, Se, $N(R^x)$, or —CH=CH—,
$Z^1$ is $C(R^x)$ or N,
W is S, Se, O or $NR^x$,
$R^1$, $R^2$ are, each independently of one another, an optionally substituted $C_{1-40}$ carbyl or hydrocarbyl group,
$U^1$ is —$C(R^x)$=, —$C(R^xR^y)$—, —$Si(R^xR^y)$—, —$N(R^x)$—, —S—, —Se—, —O— or a single bond,
$U^2$ is —$Si(R^xR^y)$—, —$N(R^x)$—, —S—, —Se—, —O— or a single bond, wherein $U^1$ and $U^2$ are not both a single bond,
$R^x$ and $R^y$ are each H or straight-chain, branched or cyclic alkyl with 1 to 30 C atoms, in which one or more non-adjacent C atoms are each optionally replaced by —O—, —S—, —C(O)—, —C(O)—O—, —O—C(O)—, O—C(O)—O—, —CH=CH— or —C≡C— and in which one or more H atoms are each optionally replaced by F, Cl, Br, I or CN,
u is 0 or 1, and
n is an integer >1.

4. A polymer according to claim 1, wherein $R^1$ and $R^2$ are selected from straight-chain, branched or cyclic alkyl with 1 to 35 C atoms, in which one or more non-adjacent C atoms are optionally replaced by —O—, —S—, —C(O)—, —C(O)—O—, —O—C(O)—, —O—C(O)—O—, —$CR^0$=$CR^{00}$— or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups $R^3$, wherein
$R^3$ is on each occurrence identically or differently F, Br, Cl, —CN, —NC, —NCO, —NCS, —OCN, —SCN, —C(O)$NR^0R^{00}$, —C(O)$X^0$, —C(O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-,
$R^0$ and $R^{00}$ are independently of each other H or optionally substituted $C_{1-40}$ carbyl or hydrocarbyl,
P is a polymerizable or crosslinkable group,
Sp is a spacer group or a single bond, and
$X^0$ is halogen.

5. A polymer according to claim 1, wherein
$R^1$ and/or $R^2$ are selected from primary alkyl or alkoxy with 1 to 30 C atoms, secondary alkyl or alkoxy with 3 to 30 C atoms, and tertiary alkyl or alkoxy with 4 to 30 C atoms, wherein in all these groups one or more H atoms are each optionally replaced by F, or
$R^1$ and/or $R^2$ are selected from aryl, aryloxy, heteroaryl and heteroaryloxy that is optionally alkylated or alkoxylated and has 4 to 30 ring atoms.

6. A mixture or blend comprising one or more polymers according to claim 1 and one or more compounds or polymers having semiconducting, charge transport, hole/electron transport, hole/electron blocking, electrically conducting, photoconducting or light emitting properties.

7. A formulation comprising one or more polymers according to claim 1, and one or more solvents.

8. A method of operating an optical, electrooptical, electronic, electroluminescent or photoluminescent component or device comprising using a charge transport, semiconducting, electrically conducting, photoconducting or light emitting material to emit light, wherein said material comprises a polymer according to claim 1.

9. An optical, electrooptical or electronic component or device comprising one or more polymers according to claim 1.

10. A component or device according to claim 9, which is selected from organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), Schottky diodes, planarizing layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

11. A component or device according to claim 9, which is an OFET or a bulk heterojunction OPV device.

12. A polymer according to claim 1, wherein W is S.
13. A polymer according to claim 1, wherein W is Se.
14. A polymer according to claim 1, wherein W is O.
15. A polymer according to claim 1, wherein W is or $NR^x$.
16. A process of preparing a polymer comprising:
coupling one or more monomers of formula Ia with each other, $$R^4—Ar^1—U—Ar^2—R^5 \quad \text{Ia}$$

wherein
U is on each occurrence, identically or differently, a unit of formula I,

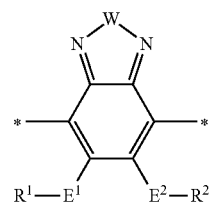

wherein
an asterisk indicates a link to an adjacent group,
W is S, Se, O or $NR^x$,
$E^1$, $E^2$ are each —O—C(O)—,
$R^x$ is H or straight-chain, branched or cyclic alkyl with 1 to 30 C atoms, in which one or more non-adjacent C atoms are each optionally replaced by —O—, —S—, —C(O)—, —C(O)—O—, —O—C(O)—, O—C(O)—O—, —CH=CH— or —C≡C— and in which one or more H atoms are each optionally replaced by F, Cl, Br, I or CN, and $R^1$, $R^2$ are, each independently of one another, an optionally substituted $C_{1-40}$ carbyl or hydrocarbyl group, $Ar^1$, $Ar^2$, are, on each occurrence identically or differently, and independently of each other, aryl or heteroaryl that is optionally substituted by one or more groups $R^3$, and one or both of $Ar^1$ and $Ar^e$ may also denote a single bond, $R^3$ is on each occurrence, identically or differently, F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$—SO$_3$H, —SO$_2$R$^0$, —OH, —NO$_2$—CF$_3$—SF$_5$, optionally substituted silyl, carbyl or hydrocarbyl with 1 to 40 C atoms that is optionally substituted and optionally comprises one or more hetero atoms, or P-Sp-, $R^0$ and $R^{00}$ are independently of each other H or optionally substituted $C_{1-40}$ carbyl or hydrocarbyl, P is a polymerizable or crosslinkable group, Sp is a spacer group or a single bond, $X^0$ is halogen, $R^4$ and $R^5$ have independently of each other one of the meanings of $R^3$, or denote H, —CH$_2$Cl, —CHO, —CH=CH$_2$, —SiR'R"R''', —SnR'R"R''', —BR'R", —B(OR')(OR"), —B(OH)$_2$, or P-Sp, and R', R" and R''' have independently of each other one of the meanings of $R^0$, and two of R', R" and R''' may also form a ring together with the hetero atom to which they are attached;

and/or coupling one or more monomers of formula Ia with one or more monomers of the formula $R^4$—$Ar^3$—$R^5$ wherein $Ar^3$ is aryl or heteroaryl that is optionally substituted by one or more groups $R^3$, in an aryl-aryl coupling reaction.

17. A process according to claim 16, wherein W is S.

* * * * *